United States Patent [19]

Magee

[11] 3,984,481

[45] Oct. 5, 1976

[54] BIS-2-SUBSTITUTED-THIOVINYL SULFONES

[75] Inventor: Philip S. Magee, Novato, Calif.

[73] Assignee: Chevron Research Company, San Francisco, Calif.

[22] Filed: Feb. 12, 1976

[21] Appl. No.: 657,676

[52] U.S. Cl. .................. 260/609 E; 260/609 R; 260/607 A; 424/337; 71/67
[51] Int. Cl.$^2$ .................................. C07C 149/10
[58] Field of Search... 260/607 A, 607 AL, 607 AR, 260/609 R, 609 E

[56] References Cited
UNITED STATES PATENTS

| | | | |
|---|---|---|---|
| 2,893,911 | 7/1959 | Raasch | 260/607 AL |
| 2,979,435 | 4/1961 | Raasch | 260/607 AL |
| 3,021,370 | 2/1962 | Bluestone | 260/609 E |
| 3,052,597 | 9/1962 | Johnston | 260/607 AL |
| 3,101,377 | 8/1963 | Bluestone et al. | 260/609 R |
| 3,117,069 | 1/1964 | Levy et al. | 260/609 R |
| 3,742,066 | 6/1973 | Tsuchihashi et al. | 260/607 AL |

OTHER PUBLICATIONS

Chem. Abst. vol. 76, (1972), pp. 58685n.

*Primary Examiner*—Lewis Gotts
*Assistant Examiner*—D. R. Phillips
*Attorney, Agent, or Firm*—G. F. Magdeburger; Dix A. Newell; Raymond Owyang

[57] ABSTRACT

Bis-(1-halo-2-alkylthioethyl) and bis-(1-halo-2-arylthioethyl) sulfones, having algicidal and fungicidal activity, are prepared by the addition of alkylsulfenyl or arylsulfenyl halides to divinyl sulfones. The sulfone products may be treated with base to produce bis-2-alkylthiovinyl or bis-2-arylthiovinyl sulfones, which also have algicidal and fungicidal activity.

4 Claims, No Drawings

BIS-2-SUBSTITUTED-THIOVINYL SULFONES

DESCRIPTION OF THE PRIOR ART

Chemical Abstracts 68 59110t (1968) and 67 108135v (1967) disclose the preparation of beta-substituted ethyl vinyl sulfones by the addition of alcohols and mercaptans to divinyl sulfone.

DESCRIPTION OF THE INVENTION

The bis-(1-halo-2-substituted-thioethyl) sulfones of the invention are represented by the formula $$RSCH_2\underset{X}{C}HSO_2\underset{X}{C}HCH_2SR \quad (I)$$

and the bis-(2-substituted-thiovinyl) sulfones of the invention are represented by the formula $$RSCH=CHSO_2CH=CHSR \quad (II)$$

wherein R is alkyl of 1 to 6 carbon atoms, phenyl or phenyl substituted with 1 to 3 of the same or different substituents selected from fluoro, chloro, bromo or nitro.

Representative alkyl R groups are methyl, ethyl, isopropyl and hexyl. Representative aryl R groups are 2-fluorophenyl, 4-chlorophenyl, 3,5-dibromophenyl, 2-nitro-4-chlorophenyl, 2-chloro-4-bromophenyl and 2,4,6-trichlorophenyl.

Preferably R is phenyl or phenyl substituted with 1 to 2 of the same or different substituents selected from fluoro, chloro, bromo or nitro. Most preferably R is phenyl substituted with 1 to 2 chloro, bromo or nitro.

Representative compounds of the invention include:
bis-(1-chloro-2-methylthioethyl) sulfone,
bis-(1-bromo-2-ethylthioethyl) sulfone,
bis-(1-bromo-2-o-fluorophenylthioethyl) sulfone,
bis-(1-chloro-2-o-chloro-p-bromophenylthioethyl) sulfone,
bis-(2-methylthiovinyl) sulfone,
bis-(2-hexylthiovinyl) sulfone,
bis-(2-o-fluorophenylthiovinyl) sulfone, and
bis-(2-o-nitro-p-chlorophenylthiovinyl) sulfone.

The bis-(1-halo-2-substituted-thioethyl) sulfones (I) are prepared by adding a sulfenyl halide (III) to divinyl sulfone (IV) and the bis-(2-substituted-thiovinyl) sulfones (II) are prepared by dehydrohalogenating the bis-(1-halo-2-substituted-thioethyl) sulfones (I) with a base, as depicted in the following reactions:

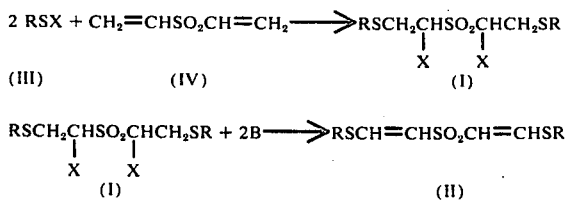

wherein R and X have the same significance as previously defined and B is a base.

Reaction (I) is conducted by reacting substantially 2 moles of the sulfenyl halide (III) per mole of the divinyl sulfone (IV) in the liquid phase at a temperature of about 0° to 100°C. Generally, an inert organic solvent, such as an alkane, a haloalkane or an aromatic compound is employed in the reaction. Reaction pressure is suitably atmospheric, subatmospheric or superatmospheric. For convenience, the reaction pressure is generally atmospheric. The reaction is generally exothermic and is completed in about 1 to 24 hours. The bis-(1-halo-2-substituted-thioethyl) sulfone product (I) is isolated and purified by conventional procedures such as extraction, filtration, chromatography, distillation or, alternatively, is used directly in reaction (2) without purification and/or isolation.

In reaction (2), the bis-(1-halo-2-substituted-thioethyl) sulfone (I) is treated with about 2 equivalents of a base. The preferred base is an organic base such as a pyridine compound, e.g., pyridine or an alkylpyridine, or a trialkylamine, e.g., triethylamine. Reaction (2) is conducted in the liquid phase at a temperature of 0° to 100°C. Generally, an inert organic diluent such as a haloalkane, e.g., dichloromethane or an aromatic hydrocarbon, e.g., benzene, is employed in the reaction. The reaction pressure is not critical, and, for convenience, the pressure is generally atmospheric. The reaction is generally complete within about 1 to 24 hours. The product (II) is isolated and purified by conventional procedures such as filtration, extraction, distillation, chromatography, etc.

UTILITY

The compounds of the invention are useful for controlling fungi, particularly plant fungal infections caused by *Botrytis cinerea*, leaf blights caused by organisms such as *Pythrium ultimum*, *Helminthosporum sativum*, *Fusarium moniliforme*, Rhizoctonia solani, Monolinia fructicola and *Uromyces phaseoli typica*. However, some fungicidal compounds of the invention may be more fungicidally active than others against particular fungi.

When used as fungicides, the compounds of the invention are applied in fungicidally effective amounts to fungi and/or their habitats, such as vegetative hosts and non-vegetative hosts, e.g., animal products. The amount used will, of course, depend on several factors such as the host, the type of fungus and the particular compound of the invention. As with most pesticidal compounds, the fungicides of the invention are not usually applied full strength, but are generally incorporated with conventional, biologically inert extenders or carriers normally employed for facilitating dispersion of active fungicidal compounds, recognizing that the formulation and mode of application may affect the activity of the fungicide. Thus, the fungicides of the invention may be formulated and applied as granules, as powdery dusts, as wettable powders, as emulsifiable concentrates, as solutions, or as any of several other known types of formulations, depending on the desired mode of application.

Wettable powders are in the form of finely divided particles which disperse readily in water or other dispersant. These compositions normally contain from about 5–80% fungicide, and the rest inert material, which includes dispersing agents, emulsifying agents and wetting agents. The powder may be applied to the soil as a dry dust, or preferably as a suspension in water. Typical carriers include fuller's earth, kaolin clays, silicas, and other highly absorbent, readily wettable, inorganic diluents. Typical wetting, dispersing or emulsifying agents include, for example: the aryl and alkylaryl sulfonates and their sodium salts; alkylamide sulfonates, including fatty methyl taurides; alkylaryl polyether alcohols, sulfated higher alcohols, and polyvinyl alcohols; polyethylene oxides, sulfonated animal and vegetable oils; sulfonated petroleum oils; fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises from 1% to 15% by weight of the fungicidal composition.

Dusts are freely flowing admixtures of the active fungicide with finely divided solids such as talc, natural clays, kieselguhr, pyrophyllite, chalk, diatomaceous earths, calcium phosphates, calcium and magnesium carbonates, sulfur, lime, flours, and other organic and inorganic solids which act as dispersants and carriers for the toxicant. These finely divided solids have an average particle size of less than about 50 microns. A typical dust formulation useful herein contains 75% silica and 25% of the toxicant.

Useful liquid concentrates include the emulsifiable concentrates, which are homogeneous liquid or paste compositions which are readily dispersed in water or other dispersant, and may consist entirely of the fungicide with a liquid or solid emulsifying agent, or may also contain a liquid carrier such as xylene, heavy aromatic naphthas, isophorone, and other nonvolatile organic solvents. For application, these concentrates are dispersed in water or other liquid carrier, and are normally applied as a spray to the area to be treated.

Other useful formulations for fungicidal applications include simple solutions of the active fungicide in a dispersant in which it is completely soluble at the desired concentration, such as acetone, alkylated naphthalenes, xylene, or other organic solvents. Granular formulations, wherein the fungicide is carried on relatively coarse particles, are of particular utility for aerial distribution or for penetration of cover-crop canopy. Pressurized sprays, typically aerosols wherein the active ingredients is dispersed in finely divided form as a result of vaporization of a low-boiling dispersant solvent carrier, such as the Freons, may also be used. All of those techniques for formulating and applying fungicides are well known in the art.

The percentages by weight of the fungicide may vary according to the manner in which the composition is to be applied and the particular type of formulation, but in general comprise 0.5 to 95% of the toxicant by weight of the fungicidal composition.

The fungicidal compositions may be formulated and applied with other active ingredients, including other fungicides, insecticides, nematocides, bactericides, plant growth regulators, fertilizers, etc.

The compounds of the invention are also useful for controlling microbiological organisms such as algae, bacteria, molds and occasionally aquatic weeds which foul aqueous industrial effluents and cooling streams, such as those occurring in the paper and food processing industries. They may also be used to control such organisms in other aqueous bodies such as lakes, streams, canals, pools and the like. When so used, a biocidal quantity of one or more of the compounds of this invention is added to the aqueous growth environment of the organisms. Usually, this dosage will range between about 0.1 to 50 ppm. In any given instance, the optimum dosage will depend upon the particular organism and aqueous body involved. For instance, when used to control algae, these compounds will usually be employed at concentrations of about 0.1 to 10 ppm. In terms of pounds of compound per acre of water one foot deep 0.1 to 10 ppm is equal to about 0.3 to 30 pounds per acre of water one foot deep. These compounds may be applied to the aqueous growth environments of such organisms as dispersible powders or in solution with water-miscible solvents.

EXAMPLE 1

Preparation of bis-2-(4-bromophenylthio)vinyl sulfone

Fifteen grams of 4-bromophenylsulfenyl chloride was added slowly to a solution of 3.0 g divinyl sulfone in 30 ml chloroform so there was no exotherm. The reaction mixture was heated under reflux for 2½ hours and then stripped. The crude product was treated with 5.2 g of triethylamine in 40 ml of benzene overnight, then filtered and stripped. The crude product was a red semisolid showing 3 spots on thin layer chromatography. The crude product, 7.0 g, was chromatographed through silica gel ($CH_2Cl_2$ eluant) to give 3.2 g bis-2-(4-bromophenylthio)vinyl sulfone as a red liquid. Thin layer chromatography of the product showed a single spot. The product and its elemental analysis is tabulated in Table I as compound No. 3.

The other compounds (except Nos. 9 or 10) tabulated in Table I were prepared by a procedure similar to that of Example 1.

EXAMPLE 2

Preparation of bis-[1-chloro-2-(4-chlorophenylthio)ethyl] sulfone 4-chlorophenylsulfenyl chloride, 7.6 g, and 2.5 g of divinyl sulfone were refluxed for 3 hours in 30 ml of methylene chloride. Stripping gave a crude oil showing 4 spots by thin layer chromatography. Purification was carried out by chromatography over silica gel. The product was eluted first with methylene chloride and then with 3:1 methylene chloride-acetone to obtain a purified fraction, 3.4 g; calcd. for $C_{16}H_{14}Cl_4O_2S_3$, S 20.2; found, S 21.5. The product is tabulated in Table I as compound No. 9.

EXAMPLE 3

Mycelial Inhibition

A number of the compounds of the present invention were evaluated for fungicidal effectiveness by means of a mycelial inhibition test. This test is designed to measure the fungitoxic activity of fungicidal chemicals in terms of their degree of inhibition of mycelium growth. Each compound to be tested was dissolved in acetone to 500 ppm concentration. Paper strips were innoculated with the particular mycelium growth by covering the paper with a potato dextrose broth culture of mycelial suspension. The innoculated papers were then placed on potato dextrose agar plates and sprayed by means of a micro sprayer with the fungicidal solution. The treated paper strips were incubated at 25°C and data is taken after 24 hours. Fungicidal activities are measured by a zone of inhibited mycelial growth from the center of the paper strip. The effectiveness of the 5 compounds tested for fungicidal activity is reported in Table II in terms of the microgram/cm$^2$ for 99% control of the fungus.

EXAMPLE 4

Algae Control

Representative compounds of the invention were tested as algicides by the following method. The algae test species were *Lemna*, *Elodea* and *Spirolina*. An acetone solution of the test compound and a small amount of an alkylarylpolyoxyethylene glycol-containing surfactant was prepared. This solution was mixed with a nutrient broth in a quantity sufficient to give a concentration of 2 ppm. A 240 ml container was filled with this mixture. A sample of the test algae was added to each container and the container was then placed in an illuminated environment and maintained at a temperature of about 20°C for incubation. The containers were observed periodically for algae growth (as compared to an untreated check). The algicidal effectiveness of the test compound was determined based on a final observation of algae growth after 7 to 10 days. The results of the test on a 0 to 100 basis — 0 indicating no effectiveness and 100 indicating complete effectiveness — are reported in Table III.

|  | Percent Aquatic Weed Control, % | | |
|---|---|---|---|
| Compound No. | Lemna | Elodea | Spirolina |
| 1 | 68 | 97 | — |
| 2 | 100 | 94 | 0 |
| 3 | 94 | 94 | 40 |
| 4 | 39 | 70 | 80 |
| 5 | 30 | 70 | 80 |
| 6 | 99 | 78 | 90 |
| 7 | 70 | 90 | 95 |
| 8 | 0 | 39 | 30 |
| 9 | 22 | 22 | 90 |
| 10 | 0 | 0 | 0 |

| | Mycelia Inhibition micrograms/cm$^2$ for 99% control | | | | |
|---|---|---|---|---|---|
| Compound No. | Pythium ultimum | Rhizoctonia solani | Aspergillus niger | Fusarium moniloforma | Botrytis cinerea |
| 1 | 0.22 | 0.9 | 0.86 | >1.7 | — |
| 2 | >1.7 | 1.5 | 1.1 | >1.7 | 1.2 |
| 3 | >1.7 | 1.4 | 0.73 | >1.7 | 1.4 |
| 4 | >1.7 | 1.2 | >1.7 | >1.7 | 0.70 |
| 5 | >1.7 | >1.7 | >1.7 | >1.7 | >1.7 |
| 6 | 0.73 | 0.50 | 0.34 | >1.7 | 0.7 |
| 7 | 0.78 | 0.97 | 1.1 | 1.0 | 0.70 |
| 8 | >1.7 | 0.88 | 0.50 | >1.7 | 1.5 |
| 9 | 0.65 | 1.5 | 1.3 | 1.3 | 1.1 |
| 10 | >1.7 | >1.7 | >1.7 | >1.7 | >1.7 |

What is claimed is:

1. A compound of the formula

RSCH = CHSO$_2$CH = CHSR wherein R is alkyl of 1 to 6 carbon atoms, phenyl or phenyl substituted with 1 to 3 of the same or different substituents selected from fluoro, chloro, bromo or nitro.

2. The compound of claim 1 wherein R is phenyl or phenyl substituted with 1 to 2 of the same or different substituents selected from chloro, bromo or nitro.

3. the compound of claim 1 wherein R is phenyl substituted with 1 to 2 chloro.

4. The compound of claim 1 wherein R is p-chlorophenyl.

| | | Compound of the formula SO$_2$(CH=CHSR)$_2$ 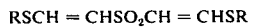 | | | | |
|---|---|---|---|---|---|---|
| | | | Elemental Analysis | | | |
| | | | Sulfur | | Halogen | |
| Compound No. | R | Physical State | Calc. | Found | Calc. | Found |
| 1 | p-Cl—φ (a) | liquid | 23.9 | 22.9 | 17.6 | 16.2 |
| 2 | m-Cl—φ | oil | 23.8 | 23.5 | 17.6 | 17.7 |
| 3 | p-Br—φ | oil | 19.5 | 18.6 | 32.5 | 33.6 |
| 4 | 2,5-Cl$_2$—φ | oil | 20.4 | 19.0 | 30.0 | 30.3 |
| 5 | p-F—φ | m.p. 85–9°C | 25.5 | 24.3 | 10.3 | 9.7 |
| 6 | p-NO$_2$—φ | semi-solid | 22.7 | 21.4 | — | — |
| 7 | 3,4-Cl$_2$—φ | oil | 20.4 | 20.2 | 30.0 | 29.2 |
| 8 | φ | oil | 28.7 | 25.3 | — | — |
| 9 | (b) | oil | 20.2 | 21.5 | — | — |
| 10 | (c) | m.p. 143–5°C | 23.6 | 23.7 | — | — |

(a) φ = phenyl
(b) bis-[1-chloro-2-(4-chlorophenylthio)ethyl] sulfone
(c) bis-2-(4-chlorophenylthio)ethyl sulfone